United States Patent [19]

Tochigi et al.

[11] Patent Number: 4,505,586
[45] Date of Patent: Mar. 19, 1985

[54] LASER RAMAN SPECTROPHOTOMETRY SYSTEM AND ADJUSTMENT THEREOF

[75] Inventors: Kenji Tochigi; Yoshiaki Hanyu; Yutaka Hiratsuka, all of Yokohama, Japan

[73] Assignee: Hitachi, Ltd., Tokyo, Japan

[21] Appl. No.: 337,818

[22] Filed: Jan. 7, 1982

[30] Foreign Application Priority Data

Jan. 14, 1981 [JP] Japan .................................. 56-3047

[51] Int. Cl.³ .............................................. G01J 3/44
[52] U.S. Cl. ................................................... 356/301
[58] Field of Search ............... 356/301, 307, 317, 318, 356/73, 417

[56] References Cited

U.S. PATENT DOCUMENTS 4,100,416 7/1978 Hirschfeld ...................... 356/307 X

OTHER PUBLICATIONS

Morhange et al., *Applied Optics*, vol. 15, No. 12, Dec. 1976, pp. 2969 and 2970.
Burgess et al., *J. Physics E. Scientific Instruments* (GB), vol. 10, No. 6, Jun. 1977, pp. 617–620.
Ignatev et al., *Sov. Tech. Phys. Lett.* vol. 4, No. 2, Feb. 1978, pp. 58 and 59.

*Primary Examiner*—F. L. Evans
*Attorney, Agent, or Firm*—Antonelli, Terry & Wands

[57] ABSTRACT

A laser Raman spectrophotometry system for analyzing a sample material by measuring spectrum of Raman scattering produced by the sample under irradiation of laser light includes a laser light source for excitation of luminescence in addition to a laser light source for the excitation of the Raman scattering, and an optical system for rendering the optical path of the laser beam for luminescence excitation to substantially coincide with the optical path of the laser beam for the Raman scattering immediately before irradiation of the specimen. Luminescence spectrum brought about by the laser beam for luminescence excitation is adjusted by adjusting the laser power to simulate the luminescence spectrum concurrently produced by the laser beam for the excitation of Raman scattering, wherein both spectra of luminescence are subtractively combined together, to thereby cancel the luminescence component and allow only the spectrum of Raman-scattered light to be measured with a correspondingly enhanced accuracy.

10 Claims, 4 Drawing Figures

LASER RAMAN SPECTROPHOTOMETRY SYSTEM AND ADJUSTMENT THEREOF

The present invention relates generally to a laser spectrophotometry system for analyzing a sample material by making use of the Raman scattering of laser light and a method of adjusting such laser spectrophotometry system. In particular, the present invention is directed to an arrangement for suppressing or mitigating adverse influence of luminescence (fluorescence) to the Raman scattering spectrophotometry.

For analyzing dusts or foreign materials of extremely fine or minute size deposited on semiconductor elements or devices, thin-film devices and others, Raman spectrophotometry in which a laser is used as a light source for excitation is known as effective means. However, in the Raman spectrophotometry, there are sometimes produced luminescence of a high intensity in addition to light scattered under the Raman effect (referred to as Raman scattering of light or Raman-scattered light) in dependence on the types of the sample materials. In particular, materials intended for industrial uses or applications which are accompanied by relatively large amounts of impurities and materials which have undergone thermal cycles, i.e. have thermal histories exhibit such a tendency that luminescence is produced at a relatively high ratio. The luminescence is usually of greater intensity and has a broader spectral width as compared with Raman-scattered light, as the result of which the Raman-scattered light is rendered indiscernible under disturbance of the luminescence, involving difficulty in carrying out the intended analysis. Besides, it is practically impossible to prepare the sample or specimen purely for the Raman spectrophotometry, since troublesome procedures such as purification and the like are required. Under these circumstances, it is necessary to impart the spectrophotometry system with a capability of eliminating influence of the luminescence.

For eliminating the disturbing luminescence produced in the Raman scattering spectrophotometry, there have been hitherto known a time-resolving spectrum analysis based on the difference of the life time between luminescence and Raman scattering and a method which is based on difference in polarization between the luminescence and the Raman-scattered light. However, the life time of luminescence is not constant but changes in the range from the order of pico-seconds at the shortest to the order of several seconds at the longest. On the other hand, the difference in polarization is not a general physical quantity which holds on every material. Thus, these methods lack flexibility and are not suited for general or universal applications.

Further, there is known a Raman spectrophotometry system which can enjoy more general applications and in which a number of light rays are simultaneously generated by a single $Ar^+$-laser, wherein the laser ray of 488.0 nm in wavelength is utilized for excitation of luminescence, while the laser ray of 514.5 nm is used for measuring superposed spectra of the Raman-scattered light and the luminescence. Through subsequent processing, a spectrum of luminescence excited by the wavelength of 488.0 nm is subtractively superposed on the spectra excited by the wavelength of 514.5 nm, thereby to obtain only a spectrum resulting from the Raman scattering. FIG. 1 shows an arrangement of the Raman spectrophotometry system suited for carrying out the method mentioned just above. Referring to the figure, a laser beam produced by a multi-mode laser light source 31 which may be constituted by an argon or $Ar^+$-laser is deflected by means of a beam bending reflector plate 32 and impinges onto a rotating disc filter 33 which is constituted by a semi-circular filter section 331 adapted to transmit therethrough the light of wavelength of 488.0 nm and another semi-circular filter section 332 which is adapted to pass therethrough the light of 514.5 nm in wavelength, both filter sections 331 and 332 being bonded together to form the disc filter 33. The disc filter 33 thus serves for extracting alternately only the rays having wavelengths of 488.0 nm and 514.5 nm from a plurality of laser rays emitted simultaneously by the laser light source 31. The light transmitted through the disc filter 33 is then collected by a condenser lens system 34 and directed to a specimen 35 for irradiation thereof. Scattering of light in the Stokes-Raman range as brought about under excitation by the light of wavelength of 514.5 nm is collected by a condenser lens system 36 and introduced to a spectrometer 37 in corporating an opto-electrical detector. An electrical signal thus produced by the spectrometer 37 is amplified by a pre-amplifier 38 and subsequently applied through a discriminator 39 to a gate circuit 40 which is opened and closed in synchronism with the rotation of the disc filter 33. To this end, the laser ray of 488.0 nm in wavelength irradiating the specimen 35 is directed to a photo-diode 42 through a filter 41 adapted to pass therethrough the wavelength of 488.0 nm. An electrical signal thus produced by the photo-diode 42 is applied to the gate circuit 40 as the synchronizing signal after having been shaped through a shaper circuit 43. The gate circuit 40 produces two separate output signals which correspond to irradiations of the specimen by the laser rays of 488.0 nm and 514.5 nm in wavelength. The separate output signals produced by the gate circuit 40 are then supplied to frequency-voltage converters 441 and 442, respectively, as can be seen from FIG. 1. The input signals to these frequency-voltage converters 441 and 442 are converted into voltage signals which are applied to a plus (+) terminal and a minus (−) terminal of a recorder 45, respectively, whereby difference between these voltage signals is recorded. The principle of the Raman spectrophotometry system of the arrangement described above is based on the known fact that the wavelength of the emitted luminescence is almost independent of the wavelength of the incident ray and that, under excitation by the ray of wavelength of 488.0 nm, only the luminescence makes appearance in the wavelength region of Stokes-Raman spectrum excited by the ray of wavelength of 514.5 nm [reference is to be made to J. F. Morhange et al "Applied Optics", 15 (12), 2969 (1976)]. However, this spectrophotometry suffers a drawback that the laser light power can not be separately adjusted because the rays of wavelengths of 488.0 nm and 514.5 nm emitted simultaneously by the single laser source are made use of for the excitation. Another disadvantage can be seen in that an improved S/N ratio can not be realized because the adjustment of luminescence level produced upon excitation by the ray of wavelength of 488.0 nm is effected by lowering the output level of the frequency-voltage converter 442 by means of an attenuator 443. In particular, when the luminescence is of high intensity, the luminescence component can not be cancelled out satisfactorily. Further, since the filters are used for selecting the laser rays of predetermined wavelengths, intensity of laser light projected to the specimen is correspondingly decreased, resulting in correspondingly reduced intensity of the Raman-scattered light as produced, which in turn means a corresponding relative increase in noise component (i.e. decrease of S/N ratio).

An object of the present invention is to provide a laser Raman spectrophotometry system which is immune to the drawbacks of the hitherto known system and capable of measuring Raman scattering spectrum with an improved S/N ratio by eliminating luminescence component which provides disturbance to the measurement of spectrum of Raman scattering.

Another object of the present invention is to provide a method of adjusting the laser Raman spectrophotometry system which method allows a luminescence component disturbing the measurement of Raman-scattering spectrum to be eliminated and thus assures the measurement of Raman scattering spectrum with an improved S/N ratio.

According to a preferred embodiment of the invention, there is provided a laser light source (hereinafter referred to as Ar+-laser) for irradiating a specimen to thereby produce continuous luminescence which disturbes measurement of spectrum of Raman-scattered light, in addition to a laser light source (hereinafter referred to as Kr+-laser) for excitation of the Raman-scattered light. Wavelength of light of the Kr+-laser is selected longer than that of the Ar+-laser for measuring Stokes-Raman scattering. The sample or specimen to be analyzed is irradiated with both of the laser beams alternately and periodically at a predetermined frequency through an optical switch. The region of wavelengths longer than that of the light of Kr+-laser is referred to as the Stokes-Raman (spectrum) region. The scattered light of the Stokes-Raman region produced under excitation by the laser beam of the Kr+-laser for exciting the Raman scattering contains a first luminescence spectrum. By irradiating the specimen with the laser beam emitted by the Ar+-laser for the luminescence excitation, a second luminescence spectrum is produced which is of a form identical with or approximating to that of the first luminescence spectrum. By superposing subtractively both the Raman-scattered light and luminescence produced by the specimen under excitation of the laser beams emitted by the Kr+-laser and the Ar+-laser, only the spectrum of Raman-scattered light produced by the specimen irradiated with light of the Kr+-laser can be measured. By adjusting intensity of the laser beam emitted by the Ar+-laser for excitation of luminescence, intensity of luminescence as produced can be controlled to coincide with the intensity of background spectrum component contained in spectrum produced upon irradiation of the specimen with the laser beam of the Kr+-laser. Both spectrum signals thus obtained undergo phase-sensitive detection at a predetermined frequency, wherein the Raman-scattered light signal containing the background component is added with the luminescence spectrum intensity signal resulted from irradiation with the Ar+-laser for luminescence excitation after polarity inversion thereof, to thereby eliminate the background or luminescence spectrum component contained in spectrum of the Raman-scattered light to be measured. In this manner, spectrum of the Raman scattering in which background component such as luminescence component and others are eliminated can be measured.

The present invention will be apparent from the following detailed description taken in conjunction with the accompanying drawings, in which.

Figure 1:
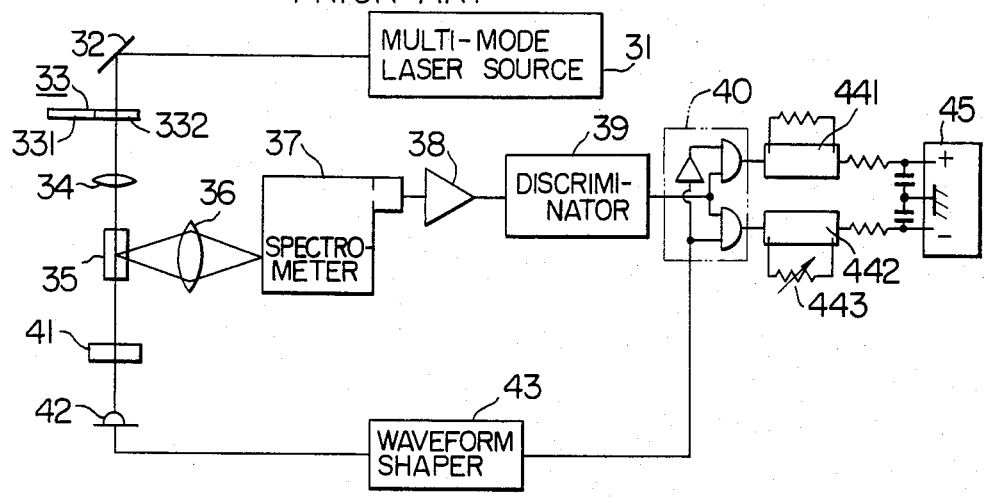
FIG. 1 illustrates an arrangement of a hitherto known laser Raman spectrophotometry system.
Figure 2:
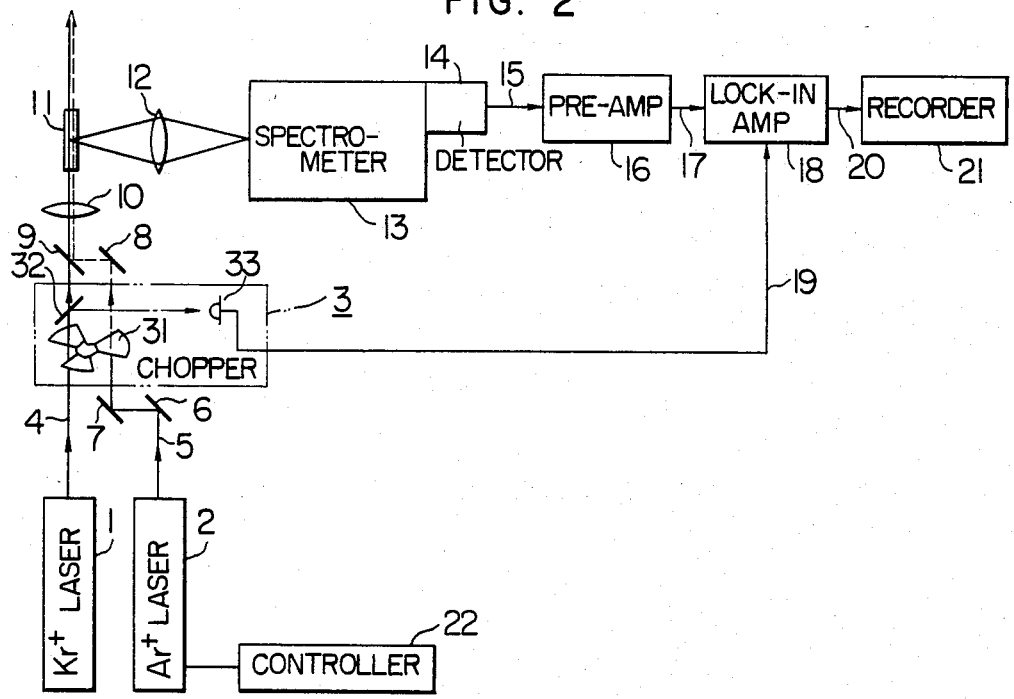
FIG. 2 illustrates an arrangement of a laser Raman spectrophotometry system according to an exemplary embodiment of the present invention.

FIG. 2 shows schematically a fundamental arrangement of the laser Raman spectrophotometry system according to an exemplary embodiment of the invention. A laser light source is constituted by a Kr+-laser source 1 adapted to emit continuously a laser light beam 4, e.g. 530.9 nm in wavelength, and an Ar+-laser source 2 adapted for emitting continuously a laser light beam 5, e.g. 488.0 nm in wavelength. The laser beam 4 is transmitted through an optical or light chopper 3, a half mirror 9 and a condenser lens system 10 to irradiate a specimen 11, while the laser beam 5 follows an optical path bent by a pair of flat mirrors 6 and 7 and is directed to the specimen 11 for irradation thereof through the optical chopper 3, a flat mirror 8, the half mirror 9 and the condenser lens system 10. The light chopper 3 serves to transmit therethrough alternately and periodically the laser beams 4 and 5. As can be seen, the laser beams 4 and 5 follow respective paths separated from each other until they reach the half mirror 9, which may be replaced by other element such as, for example, a semi-circular mirror which serves to direct the two light beams coming from different paths into the same path. With a view for allowing adjustment of the ratio in intensity of individual luminescences produced at the specimen 11 upon excitation by the laser beams 4 and 5, a power regulator or controller 22 is connected to the Ar+-laser 2.

For measuring or detecting scattered light produced by the specimen 11, there are disposed along a preselected scattering light path a condenser lens system 12, a spectrometer 13 and a detector 14 which may be incorporated in the spectrometer 13. Thus, the light produced by the specimen 11 is focused by the condenser lens system 12 and projected to the spectrometer 13 to undergo wavelength dispersion so as to detect monochromated light by the opto-electrical detector 14. An electrical output signal produced through opto-electrical conversion by the detector 14 is supplied to a pre-amplifier 16 to be amplified. An output signal 17 from the pre-amplifier 16 is applied to a signal input terminal of a lock-in amplifier 18 which has a reference signal input terminal applied with a chopping frequency reference signal 19 representative of the chopping frequency of the light chopper 3. An example of the generation of the chopping frequency reference signal 19 from the optical or light chopper 3 will be described hereinbelow. There is provided in the chopper 3 a three-blade sector 31 for alternately interrupting the laser beams 4 and 5 coming from the laser light sources 1 and 2, respectively, in such a manner that the laser beam 4 is transmitted while the laser beam 5 is interrupted. The sector wheel 31 preferably has a light transmitting part and light shutting part of equal width. When the light beam 4 from the laser source 1 is not interrupted by the three-blade sector 31, some part of the light beam 4 is split by a half mirror 32 to impinge onto an opto-electrical detector 3 such as photo-cell, photo-transistor or the like. Other beam splitter means such as prism may also be used in place of the half mirror 32. On the other hand, the remaining greater part of the light beam 4 is directed to the half mirror 9. The light input to the opto-electrical detector 33 is converted into a pulse-like electric signal which is then applied to the lock-in amplifier 18 as the reference signal 19. In the case of the illustrated system, the chopping frequency reference signal has a constant frequency (e.g. 39 Hz) which is three times as high as the rotational frequency (e.g. 13 Hz) of the three-blade sector 31. In this connection, it should be mentioned that the light chopper may be of other structure, so long as the two light beams are periodically and alternately transmitted and the reference signal which has a predetermined phase relation to one of the output light beams can be derived. The specimen 11 is thus irradiated periodically and alternately with two types of light beams 4 and 5. It is preferred that the respective duration of irradiation is the same for both the light beams 4 and 5. In the following description, it is assumed that the laser beam 4 transmitted through the light chopper 3 is in phase with the reference signal 19 as in the case of FIG. 2.

Figure 3:
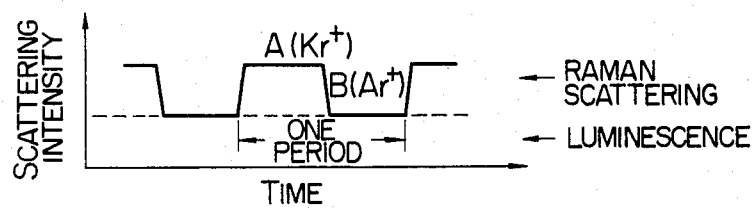
FIG. 3 is a diagram to illustrate operation of the system shown in FIG. 2.

The lock-in amplifier 18 serves to detect and amplify only the signal component of the output signal 17 from the pre-amplifier 16 that has a same frequency as that of the chopping frequency reference signal 19 derived from the light chopper 3 and a predetermined phase relation (e.g. the same phase as in the illustrated embodiment) to the signal 19. The signal component thus detected and amplified by the lock-in amplifier 18 is supplied to a recorder 21 as an output signal from the lock-in amplifier 18. The input signal to the recorder 21 is amplified therein and utilized for driving mechanically a write pen to record a signal waveform on a chart. Since the lock-in amplifier 18 detects and amplifies only the signal component of the input signal that has the same frequency as that of the reference signal 19, as described above, the input signal component having a frequency different from that of the reference signal 19 is not sampled. Further, by selecting appropriately the locked-in phase, the signal component ascribable to the laser beam 4 and the signal component ascribable to the laser beam 5 can be sampled in an appropriate phase relation. Thus, when the phase relation is so selected that both the above-mentioned signal components are in opposite phase with each other, a difference between these two signal components is detected. In this conjunction, the power of the Ar+-laser 2 is adjusted by the power controller 22 so that the intensity of luminescence detected by the detector 14 upon irradiation of the specimen 11 by the laser beam 5 to the Ar+-laser 22 is at substantially the same level with the intensity of luminescence detected by the detector 14 upon irradiation of the specimen 11 by the laser beam 4 of the Kr+-laser source 1. When the intensity of luminescence produced by the laser beam 5 is adjusted equal to the intensity of luminescence produced by the laser beam 4 in this way, the intensity of luminescence remains constant regardless of switching between the laser beams 4 and 5 by the light chopper, resulting in that only the intensity of Raman-scattered light is chopped at the chopping frequency. In other words, only the Raman-scattered light is modulated with the switching frequency of the light chopper 3. As the consequence, only the Raman-scattered light is detected and amplified by the lock-in amplifier 18 and outputted for recording by the recorder 21. Referring to FIG. 3, when the three-blade sector 31 is opened to the laser beam 4 from the Kr+-laser source 1, a signal represented by A in FIG. 3 is supplied to the input of the lock-in amplifier 18. Subsequently, when the sector 31 is closed to the laser beam 4 from the Kr+-laser source/and opened to the laser beam 5 from the Ar+-laser source 2, then a signal B is applied to the input of the lock-in amplifier 18. The signals corresponding to one period (e.g. 39 Hz) are arithmetically processed, whereby a difference signal (A-B) makes appearance at the output of the lock-in amplifier 18. Through wavelength scanning of the spectrometer 13, a spectrum of the difference (A-B) signal is obtained. The scan speed of the spectrometer should be selected lower than the speed corresponding to the time constant of the lock-in amplifier 18 in order to prevent wavelength shift in the measured spectrum. Further, the wavelength scan by the spectrometer 13 is effected at such a low speed that the wavelength shift within a period of the input signal frequency (e.g. 39 Hz) can be neglected. Theoretically, one wavelength scan by the spectrometer is enough to measure the spectrum. However, it is possible to repeat the scan and store in an external memory the results obtained from a number of repeated scans, for the purpose of improving the S/N ratio by the integration at each wavelength.

Figure 4:
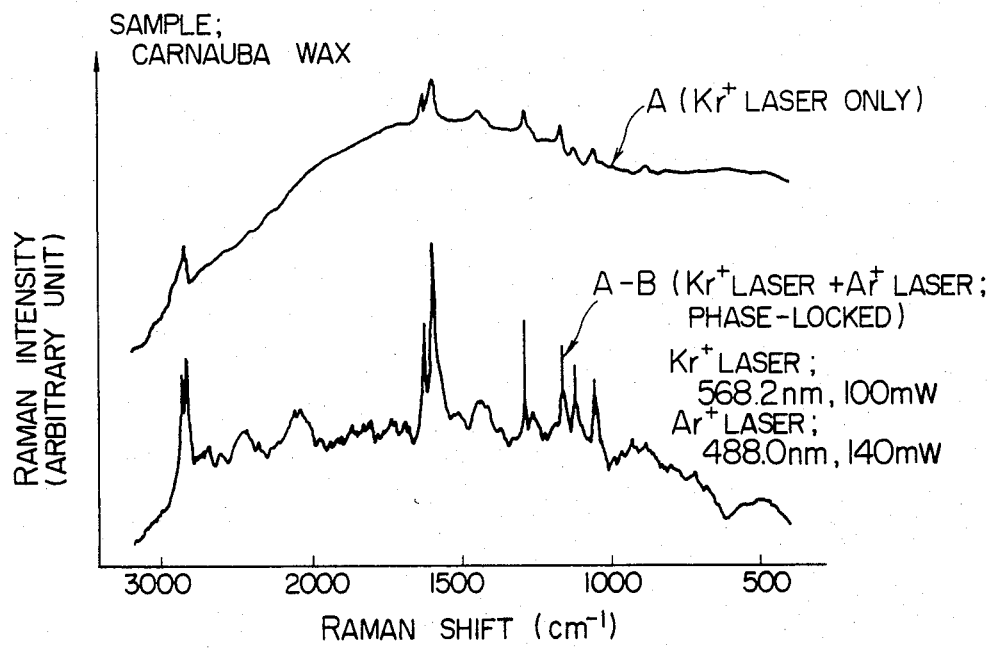
FIG. 4 shows a spectrum chart obtained from measurement of carnauba wax effected by using the laser Raman spectrophotometry system according to the invention.

FIG. 4 shows a spectrum chart actually measured by the laser Raman spectrophotometry system according to the invention in the analysis of carnauba wax contained as a mold releasing agent in a resin-mold semiconductor device. In FIG. 4, a spectrum profile curve A represents the result of measurement obtained by the hitherto known laser Raman spectrophotometry system, while a spectrum profile curve (A-B) represents the measured spectrum in which the luminescence spectral component has been eliminated according to the invention. From comparison of the curves (A-B) with A, the effect of the system according to the invention over the prior art will be readily appreciated.

Further, is should be mentioned that since random noise components which may be detected by the detector 14 is not modulated with the chopping frequency, they are neither detected nor amplified by the lock-in amplifier 18. As the consequence, noise superposed on the Raman-scattered light is decreased, to enhance the S/N ratio of the Raman scattering signal.

As is apparent from the foregoing, according to the illustrated embodiment, luminescence superposed on the Raman-scattered light can be effectively eliminated with random noise being concurrently suppressed, whereby even weak Raman scattering spectra which have not been able to be measured by the hitherto known techniques can now be measured with an improved S/N ratio according to the invention.

The present invention is not limited to the above-described embodiments. Anti-Stokes Raman scattering may be measured preferably with the wavelength of the luminescence exciting laser selected longer than that of the Raman scattering exciting laser. Further, the present invention can be applied to such weak signal measurement which is accompanied by an intense noise level, as in Brillouin scattering or the like.

We claim:

1. A laser Raman or Brillouin spectrophotometry system, comprising:

a first laser source for emitting a first laser beam of a first wavelength;

a second laser source for emitting a second laser beam of a second wavelength different from said first wavelength;

first optical means for alternately and periodically transmitting said first and second laser beams at a predetermined frequency and directing the first and second laser beams along a substantially same path to a specimen to be measured, said first optical means including reference signal means for generating a reference electrical signal having said predetermined frequency and a constant phase relation with said alternately transmitted first and second laser beams;

second optical means for detecting a light signal generated from the specimen and converting the light signal into an electrical signal; and phase-sensitive detecting means for phase-sensitively detecting the electrical signal at said predetermined frequency to detect a different signal essentially formed by subtracting a signal component corresponding to said second laser beam from a signal component corresponding to said first laser beam, the reference electrical signal being supplied to said phase-sensitive detecting means.

2. A laser Raman or Brillouin spectrophotometry system according to claim 1, further comprising:

controller means for controlling the intensity of said second laser beam emitted from said second laser source.

3. A laser Raman or Brillouin spectrophotometry system according to claim 1, wherein:

said first optical means further includes a bladed sector having a transmitting part and a shutting part of equal width.

4. A laser Raman or Brillouin spectrophotometry system according to claim 1, wherein:

said reference signal means includes a beam splitter means for splitting part of the transmitted first laser beam and light detector means for receiving and converting the split first laser beam into the reference electrical signal.

5. A laser Raman or Brillouin spectrophotometry system according to claim 2, wherein:

said controller means is capable of varying the intensity of said second laser beam in such a range that the output of said phase-sensitive detecting means is compensated for a noise component which is substantially insensitive to exciting wavelength.

6. A laser Raman or Brillouin spectrophotometry system according to claim 5, wherein said first laser souce is a $Kr^+$ laser and said second laser source is a $Ar^+$ laser.

7. A laser Raman spectrophotometry system for spectrometrically analyzing a specimen material to be examined, comprising:

a first laser light source for emitting a first laser light beam of a first wavelength for producing Raman-scattered light from said specimen;

a second laser light source for emitting a second laser light beam of a second wavelength for producing noise component light from said specimen;

means for regulating intensity of said second laser light beam;

optical switch means for transmitting therethrough said first and second laser light beams alternately and periodically at a predetermined frequency;

optical path joining means for joining optical paths of said first and second laser light beams with each other so that both of said laser light beams follow a same path thereafter, said joining means being located downstream said optical switch means;

first condenser means for focusing said laser light beams transmitted through said optical path joining means at a position of said specimen;

second condenser means for collecting light including luminescence and Raman-scattered light produced at said specimen under excitation by the laser beams focused by said first condenser means;

spectrometer means for receiving said luminescence and said Raman-scattered light transmitted through said second condenser means for dispersing into spectrum;

opto-electrical detector means for converting components of said luminescence and Raman-scattered light dispersed by said spectrometer means into corresponding electrical signal; and phase-sensitive detecting means for performing phase sensitive detection of said electrical signal produced by said opto-electrical detector means at said predetermined frequency of said optical switch means.

8. A method of adjusting a laser Raman spectrophotometry system for spectrometrically analyzing a specimen material to be examined comprising: a first laser light source for emitting a first laser light beam of a first wavelength for producing Raman-scattered light from said specimen; a second laser light source for emitting a second laser light beam of a second wavelength for producing noise component light from said specimen; means for regulating intensity of said second laser light beam; optical switch means for transmitting therethrough said first and second laser light beams alternately and periodically at a predetermined frequency; optical path joining means for joining optical paths of said first and second laser light beams with each other so that both of said laser light beams follow a same path thereafter, said joining means being located downstream of said optical switch means; first condenser means for focusing said laser light beams transmitted through said optical path joining means at a position of said specimen; second condenser means for collecting light including luminescence and Raman-scattered light produced at said specimen under excitation by the laser beams focused by said first condenser means; spectrometer means for receiving said luminescence and said Raman-scattered light transmitted through said second condenser means for dispersing into a spectrum, opto-electrical detector means for converting components of said luminescence and Raman-scattered light dispersed by said spectrometer means into corresponding electrical signal; and phase-sensitive detecting means for performing phase sensitive detection of said electrical signal produced by said opto-electrical detector means at said predetermined frequency of said switch means wherein the luminescence signal component is eliminated from the output signal produced from said phase-sensitive detecting means with only the Raman-scattered light signal component being phase-detected by adjusting intensity of luminescence produced at said specimen under excitation by said second laser light beam to the level of intensity of luminescence spectrum produced under excitation by said first laser light beam destined for exciting the Raman scattering through said means for regulating.

9. A method according to claim 8, wherein said specimen material is a material contained in a semiconductor device.

10. A method according to claim 9, wherein said specimen material is a material used in molding a semiconductor device.

* * * * *